United States Patent
Hombach et al.

(10) Patent No.: US 10,023,648 B2
(45) Date of Patent: Jul. 17, 2018

(54) ANTI-TOSO CHIMERIC ANTIGEN RECEPTOR AND ITS USE

(71) Applicant: Universitaet zu Koeln, Cologne (DE)

(72) Inventors: Andreas Hombach, Bruehl (DE); Elena Faitschuk, Cologne (DE); Hinrich Abken, Meudt (DE)

(*) Notice: Subject to any disclaimer, the term of this patent is extended or adjusted under 35 U.S.C. 154(b) by 0 days.

(21) Appl. No.: 15/166,306

(22) Filed: May 27, 2016

(65) Prior Publication Data

US 2016/0347854 A1    Dec. 1, 2016

Related U.S. Application Data

(60) Provisional application No. 62/167,419, filed on May 28, 2015.

(30) Foreign Application Priority Data

Oct. 14, 2015  (EP) .................... 15169775

(51) Int. Cl.
| | | |
|---|---|---|
| C07K 16/30 | (2006.01) | |
| A61K 35/17 | (2015.01) | |
| A61K 48/00 | (2006.01) | |
| C07K 16/28 | (2006.01) | |
| C07K 14/725 | (2006.01) | |
| C07K 14/705 | (2006.01) | |
| C12N 5/00 | (2006.01) | |
| A61K 35/12 | (2015.01) | |

(52) U.S. Cl.
CPC .............. *C07K 16/30* (2013.01); *A61K 35/17* (2013.01); *A61K 48/00* (2013.01); *C07K 14/7051* (2013.01); *C07K 14/70521* (2013.01); *C07K 16/2803* (2013.01); *C12N 5/00* (2013.01); *A61K 2035/124* (2013.01); *C07K 2317/622* (2013.01); *C07K 2317/73* (2013.01); *C07K 2317/76* (2013.01); *C07K 2319/03* (2013.01); *C07K 2319/33* (2013.01); *C07K 2319/74* (2013.01)

(58) Field of Classification Search
CPC ......... C07K 16/30; A61K 35/17; A61K 48/00
USPC .................................... 424/135.1
See application file for complete search history.

(56) References Cited

U.S. PATENT DOCUMENTS

2005/0118185 A1* 6/2005 Hombach .......... C07K 16/3046
424/185.1

FOREIGN PATENT DOCUMENTS

| WO | 2013136193 A2 | 9/2013 |
| WO | 2014164544 A1 | 10/2014 |
| WO | 2015132675 A2 | 9/2015 |

OTHER PUBLICATIONS

Grupp Stephan A. Best Practice & Research Clinical Haematology 2014, vol. 27, No. 3-4, pp. 222-228.
Pallasch Christian Philipp, et al. Leukemia & Lymphoma 2009, vol. 50, No. 3, pp. 498-501.
Nguyen Xuan-Hung, et al. Blood 2011, vol. 118, No. 3, pp. 598-608.
Tan Yin, et al. Chinese Science Bulletin, vol. 59, No. 13, 2014, pp. 1374-1385.
Pallasch CP, et al. Blood, Nov. 15, 2008; vol. 112 No. 10:4213. doi:10.1182/blood-2008-05-157255.
Gilham D.E, et al. Trends in Molecular Medicine, 2012, vol. 18 No. 7 pp. 377-384.
L. Gattinoni, et al. Nat. Rev. Immunol., Bd. 6, Nr. 5, p. 383-393, 2006.
B. Savoldo, et al. J. Clin. Invest., Bd. 121, Nr. 5, p. 1822-1826; May 2011.
S.A Grupp, et al. New England Journal of Medicine, Bd. 368, nr. 16, p. 1509-1518, 2013.
Bridgeman J.S., et al. Curr. Gene Ther. 2010, 10, 77-90.
Hombach A. et al. J. Immunotherapy, 1999, vol. 22, No. 6, pp. 473-480.
Savoldo, et al. Blood, 2007, vol. 110, No. 7, pp. 2620-2630.
Cooper, LJ, et al. Leukemia, Apr. 2004, vol. 18, No. 4, pp. 676-684.
Jensen MC, et al. Mol Ther. Apr. 2004, vol. 9, No. 4, pp. 577-586.
James SE, et al. J. Immunol. May 15, 2008; vol. 180, No. 10, pp. 7028-7038.
J.N. Kochenderfer, et al. Blood, Bd. 122, Nr. 25, p. 4129-4139, Dec. 2013.
M. Kalos, et al. Sci. Transl. Med, Bd. 3, Nr. 95, p. 95ra73, Aug. 2011.
Brentjens, et al. Blood, Nov. 3, 2011; vol. 118, No. 18, pp. 4817-4828, doi:10.1182/blood-2011-04-348540.
Cruz, et al. Blood, Bd. 122, Nr. 17, p. 2965-2973, Oct. 2013.
S.L. Maude, et al. N. Engl. J. Med., Bd. 371, Nr. 16, pp. 1507-1517, Oct. 2014.
R.J. Brenjens, et al. Sci Transl Med, Bd. 371, Nr. 177, p. 177ra38; Mar. 2013.
Giordano Attianese GM, et al. Blood, May 5, 2011, vol. 117, No. 18, pp. 4736-4745. doi:10.1182/blood-2010-10311845.
Vera J. et al. Blood, Dec. 1, 2006, 108(12)3890-7. Epub Aug. 22, 2006.
Hombach A., et al, Gene Therapy, 2010, 17, 1206-1213.
Hombach A., et al. J. Immunol., Dec. 1, 2001; vol. 167, No. 11, pp. 6123-6131.
Finney, et al. J. Immunol., Sep. 15, 1998; vol. 161, No. 6, pp. 2791-2797.
Kofler, et al. 2011, Mo. Ther. 19, 760-767.
Hombach et al. Current Molecular Medecine, 2013, vol. 13, No. 1, pp. 1-10.
Kubagawa H. et al. J. Immunol., May 1, 2015; vol. 194, No. 9, pp. 4055-4057.

(Continued)

*Primary Examiner* — Yan Xiao
(74) *Attorney, Agent, or Firm* — W&C IP

(57) ABSTRACT

In a first aspect, the present invention relates to genetically modified T-cells having a chimeric antigen receptor (CAR) in a method for adoptive cell therapy for treating TOSO$^+$ cancer, like B-cell leukemia/lymphoma, in a subject in need thereof. In particular, the present invention relates to a genetically engineered T-cell containing and expressing a specific chimeric antigen receptor being toxic to TOSO$^+$ cancer cells while being less toxic or non-toxic to TOSO$^+$ non-cancer cells, in particular, being non-toxic to normal B cells and its precursors. In a further aspect, the present invention relates to a specific chimeric antigen receptor and the nucleic acid molecule encoding the same as well as vectors and cells containing the same.

10 Claims, 4 Drawing Sheets

(56) References Cited

OTHER PUBLICATIONS

Vire, et al. J. Immunol. 2011, 187:4040-4050.
Lang P.A., et al. Cell Death and Differentiation, 2015, 22, 164-173.

* cited by examiner

SEQUENCE LISTING

```
<160> NUMBER OF SEQ ID NOS: 10

<210> SEQ ID NO 1
<211> LENGTH: 738
<212> TYPE: DNA
<213> ORGANISM: artificial sequence
<220> FEATURE:
<223> OTHER INFORMATION: 6B10
<220> FEATURE:
<221> NAME/KEY: CDS
<222> LOCATION: (1)..(738)
```

<400> SEQUENCE: 1

```
gag gtg cag ctc gtg gaa aca ggg ggg ggc ttg gtg cag cct ggg aaa      48
Glu Val Gln Leu Val Glu Thr Gly Gly Gly Leu Val Gln Pro Gly Lys
1               5                   10                  15 tct cta gaa ctc acc tgt gcc acc tca gga ttc act ttc aat acg gcc      96
Ser Leu Glu Leu Thr Cys Ala Thr Ser Gly Phe Thr Phe Asn Thr Ala
            20                  25                  30 tgg atg cac tgg gtt cgc cag tct cca gat aag cga cta gag tgg att     144
Trp Met His Trp Val Arg Gln Ser Pro Asp Lys Arg Leu Glu Trp Ile
        35                  40                  45 gct cga att aaa gac aca tct aac aat tat gca acc gac tat gtg gag     192
Ala Arg Ile Lys Asp Thr Ser Asn Asn Tyr Ala Thr Asp Tyr Val Glu
    50                  55                  60 tct atg aaa gga aga ttc acc atc tca aga gat gat tcc aaa ggt agc     240
Ser Met Lys Gly Arg Phe Thr Ile Ser Arg Asp Asp Ser Lys Gly Ser
65                  70                  75                  80 gtt aac ttg cag atg aac agc cta aaa gag gag gac act gcc act tat     288
Val Asn Leu Gln Met Asn Ser Leu Lys Glu Glu Asp Thr Ala Thr Tyr
                85                  90                  95 tac tgt act acg gat ttc tat gat ggt act tat tat tgg aat tac tgg     336
Tyr Cys Thr Thr Asp Phe Tyr Asp Gly Thr Tyr Tyr Trp Asn Tyr Trp
            100                 105                 110 ggc caa gga gtc atg gtc aca gtc tcc tca gga ggt ggt gga tcg ggc     384
Gly Gln Gly Val Met Val Thr Val Ser Ser Gly Gly Gly Gly Ser Gly
        115                 120                 125 ggt ggc ggg tcg ggt ggc ggc gga tct agc tat gag ctg atc caa cca     432
Gly Gly Gly Ser Gly Gly Gly Gly Ser Ser Tyr Glu Leu Ile Gln Pro
    130                 135                 140 cct tca gct gca gtc act ctg gga aat act gtc tca ctc act tgt gtt     480
Pro Ser Ala Ala Val Thr Leu Gly Asn Thr Val Ser Leu Thr Cys Val
145                 150                 155                 160 gga gat gaa tta cca aaa aga tat gct tat tgg tat caa caa aag cca     528
Gly Asp Glu Leu Pro Lys Arg Tyr Ala Tyr Trp Tyr Gln Gln Lys Pro
                165                 170                 175 gac cag tcc att gtg aga gtg ata tat gaa gat agc gta cgg ccc cca     576
Asp Gln Ser Ile Val Arg Val Ile Tyr Glu Asp Ser Val Arg Pro Pro
            180                 185                 190 ggc atc tct gac cga ttt tct ggg tcc agc tct ggg aca aca gcc act     624
Gly Ile Ser Asp Arg Phe Ser Gly Ser Ser Ser Gly Thr Thr Ala Thr
        195                 200                 205 ctg aca atc cgt gac gcc cag aat gag gat gag gct gat tat tac tgt     672
Leu Thr Ile Arg Asp Ala Gln Asn Glu Asp Glu Ala Asp Tyr Tyr Cys
    210                 215                 220 cag tca aca tat ggt gat gat aaa ctt tat att ttc ggc ggt gga acc     720
Gln Ser Thr Tyr Gly Asp Asp Lys Leu Tyr Ile Phe Gly Gly Gly Thr
225                 230                 235                 240 aag ctc act gtc cta ggg                                             738
Lys Leu Thr Val Leu Gly
                245
```

<210> SEQ ID NO 2
<211> LENGTH: 246
<212> TYPE: PRT
<213> ORGANISM: artificial sequence
<220> FEATURE:
<223> OTHER INFORMATION: Synthetic Construct

<400> SEQUENCE: 2

```
Glu Val Gln Leu Val Glu Thr Gly Gly Gly Leu Val Gln Pro Gly Lys
1               5                   10                  15
```

```
Ser Leu Glu Leu Thr Cys Ala Thr Ser Gly Phe Thr Phe Asn Thr Ala
         20                  25                  30

Trp Met His Trp Val Arg Gln Ser Pro Asp Lys Arg Leu Glu Trp Ile
     35                  40                  45

Ala Arg Ile Lys Asp Thr Ser Asn Asn Tyr Ala Thr Asp Tyr Val Glu
 50                  55                  60

Ser Met Lys Gly Arg Phe Thr Ile Ser Arg Asp Asp Ser Lys Gly Ser
 65                  70                  75                  80

Val Asn Leu Gln Met Asn Ser Leu Lys Glu Asp Thr Ala Thr Tyr
                 85                  90                  95

Tyr Cys Thr Thr Asp Phe Tyr Asp Gly Thr Tyr Tyr Trp Asn Tyr Trp
             100                 105                 110

Gly Gln Gly Val Met Val Thr Val Ser Ser Gly Gly Gly Ser Gly
         115                 120                 125

Gly Gly Gly Ser Gly Gly Gly Ser Ser Tyr Glu Leu Ile Gln Pro
         130                 135                 140

Pro Ser Ala Ala Val Thr Leu Gly Asn Thr Val Ser Leu Thr Cys Val
145                 150                 155                 160

Gly Asp Glu Leu Pro Lys Arg Tyr Ala Tyr Trp Tyr Gln Gln Lys Pro
                 165                 170                 175

Asp Gln Ser Ile Val Arg Val Ile Tyr Glu Asp Ser Val Arg Pro Pro
             180                 185                 190

Gly Ile Ser Asp Arg Phe Ser Gly Ser Ser Gly Thr Thr Ala Thr
         195                 200                 205

Leu Thr Ile Arg Asp Ala Gln Asn Glu Asp Glu Ala Asp Tyr Tyr Cys
     210                 215                 220

Gln Ser Thr Tyr Gly Asp Asp Lys Leu Tyr Ile Phe Gly Gly Gly Thr
225                 230                 235                 240

Lys Leu Thr Val Leu Gly
                245
```

```
<210> SEQ ID NO 3
<211> LENGTH: 2079
<212> TYPE: DNA
<213> ORGANISM: artificial sequence
<220> FEATURE:
<223> OTHER INFORMATION: chimeric antigen No 1389
<220> FEATURE:
<221> NAME/KEY: CDS
<222> LOCATION: (10)..(2079)

<400> SEQUENCE: 3 atcctctag act gcc atg gat ttt cag gtg cag att ttc agc ttc ctg cta    51
           Thr Ala Met Asp Phe Gln Val Gln Ile Phe Ser Phe Leu Leu
             1               5                  10 atc agt gcc tca gtc ata atg tct aga gag gtg cag ctc gtg gaa aca    99
Ile Ser Ala Ser Val Ile Met Ser Arg Glu Val Gln Leu Val Glu Thr
 15                  20                  25                  30 ggg ggg ggc ttg gtg cag cct ggg aaa tct cta gaa ctc acc tgt gcc   147
Gly Gly Gly Leu Val Gln Pro Gly Lys Ser Leu Glu Leu Thr Cys Ala
                 35                  40                  45 acc tca gga ttc act ttc aat acg gcc tgg atg cac tgg gtt cgc cag   195
Thr Ser Gly Phe Thr Phe Asn Thr Ala Trp Met His Trp Val Arg Gln
             50                  55                  60 tct cca gat aag cga cta gag tgg att gct cga att aaa gac aca tct   243
Ser Pro Asp Lys Arg Leu Glu Trp Ile Ala Arg Ile Lys Asp Thr Ser
 65                  70                  75 aac aat tat gca acc gac tat gtg gag tct atg aaa gga aga ttc acc   291
Asn Asn Tyr Ala Thr Asp Tyr Val Glu Ser Met Lys Gly Arg Phe Thr
```

```
                Asn Asn Tyr Ala Thr Asp Tyr Val Glu Ser Met Lys Gly Arg Phe Thr
                    80              85                  90 atc tca aga gat gat tcc aaa ggt agc gtt aac ttg cag atg aac agc        339
Ile Ser Arg Asp Asp Ser Lys Gly Ser Val Asn Leu Gln Met Asn Ser
 95              100                 105                 110 cta aaa gag gag gac act gcc act tat tac tgt act acg gat ttc tat        387
Leu Lys Glu Glu Asp Thr Ala Thr Tyr Tyr Cys Thr Thr Asp Phe Tyr
                    115                 120                 125 gat ggt act tat tat tgg aat tac tgg ggc caa gga gtc atg gtc aca        435
Asp Gly Thr Tyr Tyr Trp Asn Tyr Trp Gly Gln Gly Val Met Val Thr
                130                 135                 140 gtc tcc tca gga ggt ggt gga tcg ggc ggt ggc ggg tcg ggt ggc ggc        483
Val Ser Ser Gly Gly Gly Gly Ser Gly Gly Gly Gly Ser Gly Gly Gly
                145                 150                 155 gga tct agc tat gag ctg atc caa cca cct tca gct gca gtc act ctg        531
Gly Ser Ser Tyr Glu Leu Ile Gln Pro Pro Ser Ala Ala Val Thr Leu
                160                 165                 170 gga aat act gtc tca ctc act tgt gtt gga gat gaa tta cca aaa aga        579
Gly Asn Thr Val Ser Leu Thr Cys Val Gly Asp Glu Leu Pro Lys Arg
175                 180                 185                 190 tat gct tat tgg tat caa caa aag cca gac cag tcc att gtg aga gtg        627
Tyr Ala Tyr Trp Tyr Gln Gln Lys Pro Asp Gln Ser Ile Val Arg Val
                195                 200                 205 ata tat gaa gat agc gta cgg ccc cca ggc atc tct gac cga ttt tct        675
Ile Tyr Glu Asp Ser Val Arg Pro Pro Gly Ile Ser Asp Arg Phe Ser
                210                 215                 220 ggg tcc agc tct ggg aca aca gcc act ctg aca atc cgt gac gcc cag        723
Gly Ser Ser Ser Gly Thr Thr Ala Thr Leu Thr Ile Arg Asp Ala Gln
                225                 230                 235 aat gag gat gag gct gat tat tac tgt cag tca aca tat ggt gat gat        771
Asn Glu Asp Glu Ala Asp Tyr Tyr Cys Gln Ser Thr Tyr Gly Asp Asp
240                 245                 250 aaa ctt tat att ttc ggc ggt gga acc aag ctc act gtc cta ggg gat        819
Lys Leu Tyr Ile Phe Gly Gly Gly Thr Lys Leu Thr Val Leu Gly Asp
255                 260                 265                 270 ccc gcc gag ccc aaa tct cct gac aaa act cac aca tgc cca ccg tgc        867
Pro Ala Glu Pro Lys Ser Pro Asp Lys Thr His Thr Cys Pro Pro Cys
                275                 280                 285 cca gca cct gaa ctc ctg ggg gga ccg tca gtc ttc ctc ttc ccc cca        915
Pro Ala Pro Glu Leu Leu Gly Gly Pro Ser Val Phe Leu Phe Pro Pro
                290                 295                 300 aaa ccc aag gac acc ctc atg atc tcc cgg acc cct gag gtc aca tgc        963
Lys Pro Lys Asp Thr Leu Met Ile Ser Arg Thr Pro Glu Val Thr Cys
                305                 310                 315 gtg gtg gtg gac gtg agc cac gaa gac cct gag gtc aag ttc aac tgg       1011
Val Val Val Asp Val Ser His Glu Asp Pro Glu Val Lys Phe Asn Trp
320                 325                 330 tac gtg gac ggc gtg gag gtg cat aat gcc aag aca aag ccg cgg gag       1059
Tyr Val Asp Gly Val Glu Val His Asn Ala Lys Thr Lys Pro Arg Glu
335                 340                 345                 350 gag cag tac aac agc acg tac cgg gtg gtc agc gtc ctc acc gtc ctg       1107
Glu Gln Tyr Asn Ser Thr Tyr Arg Val Val Ser Val Leu Thr Val Leu
                355                 360                 365 cac cag gac tgg ctg aat ggc aag gag tac aag tgc aag gtc tcc aac       1155
His Gln Asp Trp Leu Asn Gly Lys Glu Tyr Lys Cys Lys Val Ser Asn
                370                 375                 380 aaa gcc ctc cca gcc ccc atc gag aaa acc atc tcc aaa gcc aaa ggg       1203
Lys Ala Leu Pro Ala Pro Ile Glu Lys Thr Ile Ser Lys Ala Lys Gly
                385                 390                 395
```

```
cag ccc cga gaa cca cag gtg tac acc ctg ccc cca tcc cgg gat gag    1251
Gln Pro Arg Glu Pro Gln Val Tyr Thr Leu Pro Pro Ser Arg Asp Glu
400                 405                 410 ctg acc aag aac cag gtc agc ctg acc tgc ctg gtc aaa ggc ttc tat    1299
Leu Thr Lys Asn Gln Val Ser Leu Thr Cys Leu Val Lys Gly Phe Tyr
415                 420                 425                 430 ccc agc gac atc gcc gtg gag tgg gag agc aat ggg cag ccg gag aac    1347
Pro Ser Asp Ile Ala Val Glu Trp Glu Ser Asn Gly Gln Pro Glu Asn
                435                 440                 445 aac tac aag acc acg cct ccc gtg ctg gac tcc gac ggc tcc ttc ttc    1395
Asn Tyr Lys Thr Thr Pro Pro Val Leu Asp Ser Asp Gly Ser Phe Phe
    450                 455                 460 ctc tac agc aag ctc acc gtg gac aag agc agg tgg cag cag ggg aac    1443
Leu Tyr Ser Lys Leu Thr Val Asp Lys Ser Arg Trp Gln Gln Gly Asn
465                 470                 475 gtc ttc tca tgc tcc gtg atg cat gag gct ctg cac aac cac tac acg    1491
Val Phe Ser Cys Ser Val Met His Glu Ala Leu His Asn His Tyr Thr
        480                 485                 490 cag aag agc ctc tcc ctg tct ccg ggt aaa aaa gat ccc aaa ttt tgg    1539
Gln Lys Ser Leu Ser Leu Ser Pro Gly Lys Lys Asp Pro Lys Phe Trp
495                 500                 505                 510 gtg ctg gtg gtg gtt ggt gga gtc ctg gct tgc tat agc ttg cta gta    1587
Val Leu Val Val Val Gly Gly Val Leu Ala Cys Tyr Ser Leu Leu Val
                515                 520                 525 aca gtg gcc ttt att att ttc tgg gtg agg agt aag agg agc agg ctc    1635
Thr Val Ala Phe Ile Ile Phe Trp Val Arg Ser Lys Arg Ser Arg Leu
    530                 535                 540 ctg cac agt gac tac atg aac atg act ccc cgc cgc ccc ggg ccc acc    1683
Leu His Ser Asp Tyr Met Asn Met Thr Pro Arg Arg Pro Gly Pro Thr
545                 550                 555 cgc aag cat tac cag ccc tat gcc ccc cca cgc gac ttc gca gcc tat    1731
Arg Lys His Tyr Gln Pro Tyr Ala Pro Pro Arg Asp Phe Ala Ala Tyr
        560                 565                 570 cgc tcc ctg aga gtg aag ttc agc agg agc gca gac gcc ccc gcg tac    1779
Arg Ser Leu Arg Val Lys Phe Ser Arg Ser Ala Asp Ala Pro Ala Tyr
575                 580                 585                 590 cag cag ggc cag aac cag ctc tat aac gag ctc aat cta gga cga aga    1827
Gln Gln Gly Gln Asn Gln Leu Tyr Asn Glu Leu Asn Leu Gly Arg Arg
                595                 600                 605 gag gag tac gat gtt ttg gac aag aga cgt ggc cgg gac cct gag atg    1875
Glu Glu Tyr Asp Val Leu Asp Lys Arg Arg Gly Arg Asp Pro Glu Met
    610                 615                 620 ggg gga aag ccg aga agg aag aac cct cag gaa ggc ctg tac aat gaa    1923
Gly Gly Lys Pro Arg Arg Lys Asn Pro Gln Glu Gly Leu Tyr Asn Glu
625                 630                 635 ctg cag aaa gat aag atg gcg gag gcc tac agt gag att ggg atg aaa    1971
Leu Gln Lys Asp Lys Met Ala Glu Ala Tyr Ser Glu Ile Gly Met Lys
        640                 645                 650 ggc gag cgc cgg agg ggc aag ggg cac gat ggc ctt tac cag ggt ctc    2019
Gly Glu Arg Arg Arg Gly Lys Gly His Asp Gly Leu Tyr Gln Gly Leu
655                 660                 665                 670 agt aca gcc acc aag gac acc tac gac gcc ctt cac atg cag gcc ctg    2067
Ser Thr Ala Thr Lys Asp Thr Tyr Asp Ala Leu His Met Gln Ala Leu
                675                 680                 685 ccc cct cgc taa                                                    2079
Pro Pro Arg
```

<210> SEQ ID NO 4
<211> LENGTH: 689
<212> TYPE: PRT

<213> ORGANISM: artificial sequence
<220> FEATURE:
<223> OTHER INFORMATION: Synthetic Construct

<400> SEQUENCE: 4

```
Thr Ala Met Asp Phe Gln Val Gln Ile Phe Ser Phe Leu Leu Ile Ser
1               5                   10                  15

Ala Ser Val Ile Met Ser Arg Glu Val Gln Leu Val Glu Thr Gly Gly
            20                  25                  30

Gly Leu Val Gln Pro Gly Lys Ser Leu Glu Leu Thr Cys Ala Thr Ser
        35                  40                  45

Gly Phe Thr Phe Asn Thr Ala Trp Met His Trp Val Arg Gln Ser Pro
    50                  55                  60

Asp Lys Arg Leu Glu Trp Ile Ala Arg Ile Lys Asp Thr Ser Asn Asn
65                  70                  75                  80

Tyr Ala Thr Asp Tyr Val Glu Ser Met Lys Gly Arg Phe Thr Ile Ser
                85                  90                  95

Arg Asp Asp Ser Lys Gly Ser Val Asn Leu Gln Met Asn Ser Leu Lys
            100                 105                 110

Glu Glu Asp Thr Ala Thr Tyr Tyr Cys Thr Thr Asp Phe Tyr Asp Gly
        115                 120                 125

Thr Tyr Tyr Trp Asn Tyr Trp Gly Gln Gly Val Met Val Thr Val Ser
    130                 135                 140

Ser Gly Gly Gly Gly Ser Gly Gly Gly Ser Gly Gly Gly Gly Ser
145                 150                 155                 160

Ser Tyr Glu Leu Ile Gln Pro Pro Ser Ala Ala Val Thr Leu Gly Asn
                165                 170                 175

Thr Val Ser Leu Thr Cys Val Gly Asp Glu Leu Pro Lys Arg Tyr Ala
            180                 185                 190

Tyr Trp Tyr Gln Gln Lys Pro Asp Gln Ser Ile Val Arg Val Ile Tyr
        195                 200                 205

Glu Asp Ser Val Arg Pro Pro Gly Ile Ser Asp Arg Phe Ser Gly Ser
    210                 215                 220

Ser Ser Gly Thr Thr Ala Thr Leu Thr Ile Arg Asp Ala Gln Asn Glu
225                 230                 235                 240

Asp Glu Ala Asp Tyr Tyr Cys Gln Ser Thr Tyr Gly Asp Asp Lys Leu
                245                 250                 255

Tyr Ile Phe Gly Gly Thr Lys Leu Thr Val Leu Gly Asp Pro Ala
            260                 265                 270

Glu Pro Lys Ser Pro Asp Lys Thr His Thr Cys Pro Pro Cys Pro Ala
        275                 280                 285

Pro Glu Leu Leu Gly Gly Pro Ser Val Phe Leu Phe Pro Pro Lys Pro
    290                 295                 300

Lys Asp Thr Leu Met Ile Ser Arg Thr Pro Glu Val Thr Cys Val Val
305                 310                 315                 320

Val Asp Val Ser His Glu Asp Pro Glu Val Lys Phe Asn Trp Tyr Val
                325                 330                 335

Asp Gly Val Glu Val His Asn Ala Lys Thr Lys Pro Arg Glu Glu Gln
            340                 345                 350

Tyr Asn Ser Thr Tyr Arg Val Val Ser Val Leu Thr Val Leu His Gln
        355                 360                 365

Asp Trp Leu Asn Gly Lys Glu Tyr Lys Cys Lys Val Ser Asn Lys Ala
    370                 375                 380

Leu Pro Ala Pro Ile Glu Lys Thr Ile Ser Lys Ala Lys Gly Gln Pro
```

```
        385                 390                 395                 400
Arg Glu Pro Gln Val Tyr Thr Leu Pro Pro Ser Arg Asp Glu Leu Thr
                    405                 410                 415

Lys Asn Gln Val Ser Leu Thr Cys Leu Val Lys Gly Phe Tyr Pro Ser
                420                 425                 430

Asp Ile Ala Val Glu Trp Glu Ser Asn Gly Gln Pro Glu Asn Asn Tyr
            435                 440                 445

Lys Thr Thr Pro Pro Val Leu Asp Ser Asp Gly Ser Phe Phe Leu Tyr
        450                 455                 460

Ser Lys Leu Thr Val Asp Lys Ser Arg Trp Gln Gln Gly Asn Val Phe
465                 470                 475                 480

Ser Cys Ser Val Met His Glu Ala Leu His Asn His Tyr Thr Gln Lys
                485                 490                 495

Ser Leu Ser Leu Ser Pro Gly Lys Lys Asp Pro Lys Phe Trp Val Leu
                500                 505                 510

Val Val Val Gly Gly Val Leu Ala Cys Tyr Ser Leu Leu Val Thr Val
            515                 520                 525

Ala Phe Ile Ile Phe Trp Val Arg Ser Lys Arg Ser Arg Leu Leu His
        530                 535                 540

Ser Asp Tyr Met Asn Met Thr Pro Arg Arg Pro Gly Pro Thr Arg Lys
545                 550                 555                 560

His Tyr Gln Pro Tyr Ala Pro Pro Arg Asp Phe Ala Ala Tyr Arg Ser
                565                 570                 575

Leu Arg Val Lys Phe Ser Arg Ser Ala Asp Ala Pro Ala Tyr Gln Gln
                580                 585                 590

Gly Gln Asn Gln Leu Tyr Asn Glu Leu Asn Leu Gly Arg Arg Glu Glu
            595                 600                 605

Tyr Asp Val Leu Asp Lys Arg Gly Arg Asp Pro Glu Met Gly Gly
        610                 615                 620

Lys Pro Arg Arg Lys Asn Pro Gln Glu Gly Leu Tyr Asn Glu Leu Gln
625                 630                 635                 640

Lys Asp Lys Met Ala Glu Ala Tyr Ser Glu Ile Gly Met Lys Gly Glu
                645                 650                 655

Arg Arg Arg Gly Lys Gly His Asp Gly Leu Tyr Gln Gly Leu Ser Thr
                660                 665                 670

Ala Thr Lys Asp Thr Tyr Asp Ala Leu His Met Gln Ala Leu Pro Pro
            675                 680                 685

Arg

<210> SEQ ID NO 5
<211> LENGTH: 702
<212> TYPE: DNA
<213> ORGANISM: artificial
<220> FEATURE:
<223> OTHER INFORMATION: synthetic nucleic acid sequence

<400> SEQUENCE: 5
gatcccgccg agcccaaatc tcctgacaaa actcacacat gcccaccgtg cccagcacct      60
ccagtcgcgg gaccgtcagt cttcctcttc cccccaaaac ccaaggacac cctcatgatc     120
tcccggaccc ctgaggtcac atgcgtggtg gtggacgtga gccacgaaga ccctgaggtc     180
aagttcaact ggtacgtgga cggcgtggag gtgcataatg ccaagacaaa gccgcgggag     240
gagcagtaca acagcacgta ccgggtggtc agcgtcctca ccgtcctgca ccaggactgg     300
ctgaatggca aggagtacaa gtgcaaggtc tccaacaaag ccctcccagc ccccatcgag     360
```

```
aaaaccatct ccaaagccaa agggcagccc cgagaaccac aggtgtacac cctgccccca      420
tcccgggatg agctgaccaa gaaccaggtc agcctgacct gcctggtcaa aggcttctat      480
cccagcgaca tcgccgtgga gtgggagagc aatgggcagc cggagaacaa ctacaagacc      540
acgcctcccg tgctggactc cgacggctcc ttcttcctct acagcaagct caccgtggac      600
aagagcaggt ggcagcaggg gaacgtcttc tcatgctccg tgatgcatga ggctctgcac      660
aaccactaca cgcagaagag cctctccctg tctccgggta aa                         702
```

<210> SEQ ID NO 6
<211> LENGTH: 213
<212> TYPE: DNA
<213> ORGANISM: artificial
<220> FEATURE:
<223> OTHER INFORMATION: synthetic sequence

<400> SEQUENCE: 6

```
gatcccaaat tttgggtgct ggtggtggtt ggtggagtcc tggcttgcta tagcttgcta       60
gtaacagtgg cctttattat tttctgggtg aggagtaaga ggagcaggct cctgcacagt      120
gactacatga acatgactcc ccgccgcccc gggcccaccc gcaagcatta ccaggcctat      180
gccgccgcac gcgacttcgc agcctatcgc tcc                                   213
```

<210> SEQ ID NO 7
<211> LENGTH: 342
<212> TYPE: DNA
<213> ORGANISM: artificial
<220> FEATURE:
<223> OTHER INFORMATION: synthetic sequence

<400> SEQUENCE: 7

```
ctgagagtga agttcagcag gagcgcagac gcccccgcgt accagcaggg ccagaaccag       60
ctctataccg agctcaatct aggacgaaga gaggagtacg atgttttgga caagagacgt      120
ggccgggacc ctgagatggg gggaaagccg agaaggaaga accctcagga aggcctgtac      180
aatgacctgc agaaagataa gatggcggag gcctacagtg agattgggat gaaaggcgag      240
cgccggaggg gcaaggggca cgatggcctt taccagggtc tcagtacagc caccaaggac      300
acctacgacg cccttcacat gcaggccctg ccccctcgct aa                         342
```

<210> SEQ ID NO 8
<211> LENGTH: 129
<212> TYPE: DNA
<213> ORGANISM: artificial
<220> FEATURE:
<223> OTHER INFORMATION: synthetic sequence

<400> SEQUENCE: 8

```
cgactgaaga tccaagtgcg aaaggcagct ataaccagct atgagaaatc agatggtgtt       60
tacacgggcc tgagcaccag gaaccaggag acttacgaga ctctgaagca tgagaaacca      120
ccacagtag                                                              129
```

<210> SEQ ID NO 9
<211> LENGTH: 25
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (8)..(20)

```
<223> OTHER INFORMATION: SVFLFPPKPKDTL

<400> SEQUENCE: 9

Pro Glu Leu Leu Gly Gly Pro Xaa Xaa Xaa Xaa Xaa Xaa Xaa Xaa Xaa
1               5                   10                  15

Xaa Xaa Xaa Xaa Met Ile Ser Arg Thr
            20                  25

<210> SEQ ID NO 10
<211> LENGTH: 24
<212> TYPE: PRT
<213> ORGANISM: artificial
<220> FEATURE:
<223> OTHER INFORMATION: synthetic peptide
<220> FEATURE:
<221> NAME/KEY: MISC_FEATURE
<222> LOCATION: (7)..(19)
<223> OTHER INFORMATION: SVFLFPPKPKDTL

<400> SEQUENCE: 10

Pro Pro Val Ala Gly Pro Xaa Xaa Xaa Xaa Xaa Xaa Xaa Xaa Xaa
1               5                   10                  15

Xaa Xaa Xaa Met Ile Ala Arg Thr
            20
```

ANTI-TOSO CHIMERIC ANTIGEN RECEPTOR AND ITS USE

In a first aspect, the present invention relates to genetically modified T-cells having a chimeric antigen receptor (CAR) in a method for adoptive cell therapy for treating TOSO+ cancer, like B-cell leukemia/lymphoma, in a subject in need thereof. In particular, the present invention relates to a genetically engineered T-cell containing and expressing a specific chimeric antigen receptor being toxic to TOSO+ cancer cells while being less toxic or non-toxic to TOSO+ non-cancer cells, in particular, being non-toxic to normal B cells and its precursors. In a further aspect, the present invention relates to a specific chimeric antigen receptor and the nucleic acid molecule encoding the same as well as vectors and cells containing the same.

PRIOR ART

Adoptive cell therapy for malignant diseases is showing promise in recent early phase trials in the treatment of B cell leukemia/lymphoma. Genetically engineered with a tumor-specific chimeric antigen receptor (CAR), patient's T cells produce lasting and complete leukemia regression. However, treatment is associated with some toxicity which needs our attention and the field still faces some hurdles at the scientific, technologic, and clinical level. Usually, patient derived T-cells are engineered ex vivo to express a recombinant T-cell (TCR), alternatively, a Chimeric Antigen Receptor (CAR). Said CAR is typically composed of an extracellular antigen binding domain derived from an antibody and an intracellular T-cell activation domain derived from a signaling T-cell receptor endodomain. In contrast to the physiological TCR, the CAR is composed of one single polypeptide chain that combines antigen binding via the extracellular moiety with a T-cell activation machinery provided by the intracellular signaling moiety. Thus, due to the antibody derived binding domain, CAR modified T-cells recognize their target, usually, a cell surface antigen, independently of presentation by the Major Histocompatibility Complex (MHC). Further, chimeric antigen receptor modified T-cells are not compromised by tumor cell variants with lowered or deficient antigen processing which represents a commonly observed mechanism of tumor immune escape.

CARs are in the focus of extensive research activities during the recent years, in particular, since refractory advanced chronic lymphatic leukemia (CLL) was turned into complete and lasting remission by treatment with genetically engineered T cells (J. N. Kochenderfer, et al., *Blood*, Bd. 122, Nr. 25, S. 4129-4139, December 2013.). Patient's T cells were redirected towards leukemic cells by an engrafted chimeric antigen receptor (CAR) with specificity for CD19 ("CTL019"). With little alternatives left but still sensitive to some chemotherapeutics, patients received CD19 specific CAR T cells in a split-dose manner within 3 days up to a total dose of $1.1 \times 10^9$ CART cells, the lowest dose was $1.4 \times 10^7$ CART cells (M. Kalos, et al., *Sci Transl Med*, Bd. 3, Nr. 95, S. 95ra73, August 2011.). T cell therapy produced remission in 12 out of 23 CLL patients, with 6 complete responses remaining disease free to date. The induction of lasting remissions make the CD19 targeting CAR T cell trial (NCT01029366) a milestone in the CAR field, although the trial at University of Pennsylvania is not the first and not the only CAR T cell study to be launched in humans. Other centers including Sloan Kettering Memorial Institute (Brentjens et al., Blood. 2011 Nov. 3; 118(18): 4817-28. doi: 10.1182/blood-2011-04-348540) and Baylor College of Medicine (Cruz et al., *Blood*, Bd. 122, Nr. 17, S. 2965-2973, October 2013) successfully treated CLL patients with anti-CD19 CART cells as well. In one of the follow up trials targeting pediatric acute lymphoblastic leukemia (ALL) with CTL019 cells, the first treated patient went into complete and lasting remission. Taken pediatric and adult ALL together, 27/30 complete remissions were achieved, 19 patients remain in remission to date and 6 patients experienced relapses (NCT01626495, NCT01029366) (e.g. S. L. Maude, et al., *N. Engl. J. Med.*, Bd. 371, Nr. 16, S. 1507-1517, Okt. 2014) These and other leukemia/lymphoma trials demonstrate the outstanding potential of CAR T cells. Since the first clinical trial with anti-CD19 CAR T cells in B cell malignancies, more than 70 patients were treated in different trials in the US.

Although the trial design can hardly be compared, some basic lines for the therapeutic efficacy become visible. First, there is no correlation between the number of infused CAR T cells or patients' tumor burden and the clinical outcome, pointing to the high proliferative potential and serial killing capacities of CAR T cells after administration (R. J. Brentjens, et al., *Sci Transl Med*, Bd. 5, Nr. 177, S. 177ra38, March 2013). Second, lymphodepletion prior CART cell therapy seems to be mandatory to shape a favorite environment for the adoptively transferred T cells, to eradicate suppressor cells and to make a severely affected bone marrow more susceptible for T cell penetration (L. Gattinoni, et al., *Nat. Rev. Immunol.*, Bd. 6, Nr. 5, S. 383-393, 2006). Third, costimulation to push the transferred T cells to full activation is a prerequisite for their persistence and the establishment of a specific memory, both required for a lasting anti-tumor response. In this context, so called second generation CARs with costimulatory and primary CD3ζ signaling co-integrated into the same CAR molecule are an indubitable advantage over first generation CARs with the CD3ζ signal only (B. Savoldo, et al., *J. Clin. Invest.*, Bd. 121, Nr. 5, S. 1822-1826, Mai 2011).

However, substantial risks and toxicities become obvious to be an imminent part of anti-CD19 CAR T cell therapy. Among them, B cell aplasia as a major consequence of "on-target, off-tumor" toxicity was observed in all patients treated so far. B-cell depletion needs live-long clinical attention and is currently managed by immunoglobulin replacement therapy. The choice for a suitable target remains most challenging with respect to CAR T cell associated toxicity and selectivity in cancer cell targeting. Broad clinical application of adoptive cell therapy in cancer requires CARs with more selectivity for cancer cells and less targeting healthy cells.

Numerous efforts were made to identify such targets suitable for CAR therapy and to design CARs suitable for selective targeting. The current efforts include low affinity binding and combinatorial recognition of two antigens on the same target cell. In the context of leukemic cell targeting, combinatorial recognition of CD5 and CD19 by two CARs may prevent B cell aplasia while targeting leukemic cells.

While CAR targeting is specific for the cognate antigen, mutant cancer cells with down-regulated or mutated antigens are invisible to CAR T cells. Loss of target occurs under selective pressure and was observed in a recent trial for CAR T cell treatment of B-ALL (S. A. Grupp. et al., *New England Journal of Medicine*, Bd. 368, Nr. 16, S. 1509-1518, 20132013). To prevent the relapse of antigen-loss cancer cells, the use of bispecific CAR T cells might be an option, either by engineering with two CARs, each of different specificity, or with one CAR with two specificities.

Alternatively, a mixture of two T cell populations, each expressing a CAR with a defined specificity, may be used.

Taken together, a significant drawback of the CD19 CAR T cell therapy of B cell derived leukemia and lymphoma is the elimination of the healthy CD19+ B cells which requires life-long clinical attention and immunoglobulin substitution. Although tremendous effort is currently made, no preferential targeting of leukemia/lymphoma was achieved so far.

In recent years, efforts have been done in the optimization of the CAR design, (for review see e.g. Bridgeman J. S., et al., Curr Gene Ther 2010, 10, 77-90). However, many challenges remain, in particular, the necessity of a more effected anti-tumor response and prolonging T-cell survival allowing long term T-cell persistence of said engineered T-cells in the body. The selectivity in targeting cancer cells versus healthy cells is still a major issue, in particular when targeting leukemia/lymphoma. In addition, the co-stimulatory signals required for sustaining T-cell persistence and activation during clinical application remain to be identified. Hence, there is ongoing work on optimizing CAR for various approaches including adaptive immunotherapy.

Already in 1999, Hombach A., et al., J. Immunotherapy, 1999, 22(6), 473-480, describe a chimeric T-cell receptor with specificity for the Hodgkin's lymphoma associated CD30 antigen. It is identified herein, that specific crosslinking of the chimeric receptor by binding to CD30 induces MHC-unrestricted cellular toxicity against CD30+ target cells but not against CD30-cells. Since CD30 is expressed by tumor cells, although also by normal activated B-cells, it was hesitated to use CD30 as a target for the elimination of leukemia/lymphoma cells. The assumption was sustained by the report by Savoldo et al., Blood, 2007, 110(7), 2620-2630, which demonstrates that CAR T-cells exhibit cytolysis of B-cell type lymphoblastoid cell lines (LCL cell lines). The CAR used therein is a "first generation" CAR.

For the treatment of leukemia/lymphoma, CARs directed towards other targets were reported including CD19 (Cooper L J, et al., Leukemia. 2004 April; 18(4):676-84), CD20 (Jensen M C, et al., Mol Ther. 2004 April; 9(4):577-86), CD22, (James S E, et. al., J Immunol. 2008 May 15; 180(10):7028-38), CD23 (Giordano Attianese G M, et al., Blood. 2011 May 5; 117(18):4736-45. doi: 10.1182/blood-2010-10-311845), Ig kappa light chain (Vera J, et al., Blood. 2006 Dec. 1; 108(12):3890-7. Epub 2006 Aug. 22).

Hombach A. et al., Gene Therapy, 2010, 17, 1206-1213 describe the modification of the IgG1 Fc spacer domain in the extracellular CAR moiety of avoiding off-target activation by Fc receptor+ cells and unintended initiation of an innate immune response.

Hombach et al. (J Immunol. 2001 Dec. 1; 167(11):6123-31.) and Finney et al. (J Immunol. 1998 Sep. 15; 161(6): 2791-7.) report to combine the CD3zeta and the CD28 intracellular domain in the same CAR molecule to provide costimulation upon target engagement. As a result the T cell response is improved with respect to cytokine release, amplification, persistence and lysis among other functions. Kofler et al., 2011, Mol. Ther. 19, 760-767 describe a CAR molecule having a modified CD28 endodomain combined with a CD3zeta endodomain and an antibody derived scFv ectodomain specific for CEA. It is described therein that a deletion of the lck binding moiety in the CD28 CAR endodomain improves redirected anti-tumor activity in the presence of T-regulatory (Treg) cells without impairment of interferon-gamma (IFN-g) secretion, proliferation and cytolysis. It is speculated that the CAR with the modified CD28 endodomain expedite the implementation of adaptive T-cell therapy in patients with a variety of cancer types that are heavily infiltrated by Treg cells.

In addition, a summary of adoptive therapy of cancer with CAR redirected T-cells is provided in Hombach et al., Current Molecular Medicine, 2013, 13(1), 1-10. Therein, the CAR effects are summarized including co-stimulation activity as well as improvement and prolongation of the redirected anti-tumor T-cell response. In addition, the adverse effects of this kind of adaptive therapy are described including "cytokine storm" and "T-cell repression".

Beside the beneficial effect of the CAR expressing T-cells in adoptive therapy, adverse side effects are known which presently hinder favorite development of respective therapy as mentioned above. As described in the referenced documents, development of CARs result in second and third generation CARs, which harbor one or two costimulatory signaling domains, trying to overcome the same. However, a remaining problem of CAR based adoptive therapy is that the engineered T-cells expressing the CAR do not discriminate between malignant cells (cancer cells) and healthy cells (non-tumor cells) while both types of cells express the same antigenic determinant of the antigen binding domain present in the CAR molecule.

Hence, a major problem of cancer-specific CAR T-cell therapy is to minimize side effects on healthy tissues. Further, a more selective targeting of the tumor cells is needed. In particular, selective targeting of lymphoma/leukemia is needed in order to avoid immune therapy induced deficiency which persists as long as the CAR T cells are active.

TOSO, also known as Fas-inhibitory molecule-3 (FAIM3), is a transmembrane-protein and the function has not yet been fully elucidated (Kubagawa H, et al., J Immunol. 2015 May 1; 194(9):4055-7). Inhibition of Fas-mediated apoptosis is mediated by binding of the C-terminal domain of TOSO with FADD. TOSO is also described as the IgM Fc receptor (FcμR) (Vire et al., J Immunol 2011, 187: 4040-4050).

TOSO is overexpressed in B-cell leukemia including B-CLL. Evidences were reported that TOSO is an anti-apoptotic factor in CLL pathogenesis, triggered by BCR signaling and further regulated by stroma interaction via the CD40 molecule.

Recently, Lang P. A., et. al., (Cell Death and Differentiation, 2015, 22, 164-173) described that TOSO has an essential role in the differentiation and maturation of inflammatory dendritic cells.

Further, WO 2013/136193 claims and suggests to treat cancer using soluble TOSO. WO 2014/164544, see SEQ ID No. 2, discloses a CAR having 81.8% identity to present SEQ ID No. 4. Grupp Stephan A., BEST PRACTICE & RESEARCH CLINICAL HAEMATOLOGY 2014, vol. 27, no. 3-4, pages 222-228, discloses treatment of CLL using anti-CD19 CAR. Pallasch Christian Philipp et al, LEUKEMIA & LYMPHOMA 2009, vol. 50, no. 3, pages 498-501 discloses high levels of TOSO expression in CLL. Further studies will reveal the functional context of TOSO in CLL and B cell biology. Surface expression of TOSO will enable antibody-based targeting of this novel CLL-antigen.

Nguyen Xuan-Hung et al, BLOOD 2011, vol. 118, no. 3, pages 598-608, discloses that the antiapoptotic function of Toso could be blocked by a Toso-specific monoclonal antibody, opening up new therapeutic prospects for the treatment of immune disorders and hematologic malignancies. Vire Bérengère et al, JOURNAL OF IMMUNOLOGY 2011, vol. 187, no. 8, pages 4040-4050, discloses that TOSO/FAIM3 recently has been identified as the long-sought-after FcR for IgM (Fc[mu]R). Fc[mu]R is expressed on chronic lymphocytic leukemia (CLL) cells. FC[mu]R deserves study as a potential pathway for the delivery of therapeutic Ab-drug conjugates into CLL cells. Tan Yi et al, CHINESE SCIENCE BULLETIN, vol. 59, no. 13, 2014, pages 1374-1385 discloses that treatment of activated T cells with anti-TOSO blocking mAb promoted T cell AICD in in vitro. The data indicate the anti-apoptotic effect of TOSO in T cell AICD and open up new therapeutic prospects for the treatment of hematologic malignancies and immune disorders. WO 2015/132675 claims and suggests to treat cancer using an inhibitor of TOSO activity. The claimed treatment is exemplified with soluble TOSO-Fc.

BRIEF DESCRIPTION OF THE PRESENT INVENTION

In a first aspect, the present invention relates to a method of adoptive cell therapy for treating TOSO+ cancer, including TOSO+ leukemia or TOSO+ lymphoma, in a subject in need thereof comprising the step of administering T-cells with a chimeric antigen receptor whereby the chimeric antigen receptor contains the following domains starting from the N-terminus to the C-terminus: an anti-TOSO single-chain antibody domain, in particular, 6B10, or a homolog thereof binding specifically to TOSO having at least 70% identity with SEQ ID No. 2; a transmembrane domain; and a cytoplasmatic signaling domain; optionally a spacer domain between the anti-TOSO single chain antibody domain and the transmembrane domain characterized in that said T-cell with the chimeric antigen receptor initiates or augments an immune response against or is toxic to TOSO+ cancer cells, in particular, TOSO+ leukemia cells or TOSO+ lymphoma cells while being non-toxic or less toxic to TOSO+ non-tumor (healthy) cells in said subject. Any other antibody or polypeptide binding to TOSO or a TOSO ligand can alternatively be used as binding domain of the chimeric antigen receptor.

In particular, the present invention relates to a T-cell expressing the CAR which is a polypeptide of SEQ. ID No. 4 encoded by a nucleic acid of Seq. ID. No. 3 or a homolog thereof.

In a further aspect, the present invention relates to the method using T-cells with a chimeric antigen receptor according to the present invention for treating TOSO+ cancer in a subject in need thereof. In particular, the TOSO+ cancer is any one of B- or T-cell derived leukemia/lymphoma, in particular chronic lymphocytic leukemia, Hodgkin's lymphoma, non-Hodgkin's lymphoma, anaplastic large cell lymphoma, acute and chronic lymphocytic leukemia, cutaneous lymphoma, mycosis fungoides, Sézary lymphoma, lymphoproliferative diseases, systemic mastocytosis, stem cell derived malignancies, cancer stem cells or others.

Moreover, the present invention relates to a polypeptide of SEQ ID No. 4 or a homolog thereof having at least 90% identity with Seq. ID. No. 4 whereby said polypeptide or a homolog thereof when being expressed in a T-cell as a chimeric antigen receptor displays a toxic effect on TOSO+ cancer cells while being non-toxic or less toxic on TOSO+ non-cancer cells.

In addition, the present invention relates to a nucleic acid molecule encoding the polypeptide according to the present invention as well as a vector comprising said nucleic acid sequence, e.g. Seq. ID. No. 3. Moreover, a cell, cell line or host cell containing said nucleic acid sequence or said vector is provided as well as a kit or system containing the vector or a cell, cell line or a host cell containing said vector or said nucleic acid molecule or containing said nucleic acid molecule.

[B] Detection of TOSO on the cell surface of blood mononuclear cells obtained from B-CLL patients compared to healthy donor blood cells. Cells were stained with anti-human-CD5-APC antibody, anti-CD19-FITC antibody to identify B cells and B-CLL cells, followed by staining with the FITC-conjugated anti-TOSO antibody (black line). An isotype-matched FITC-conjugated antibody served as control (dotted line). The dot plot and the histograms show the analyses of cells of a representative healthy donor.

Figure 3:
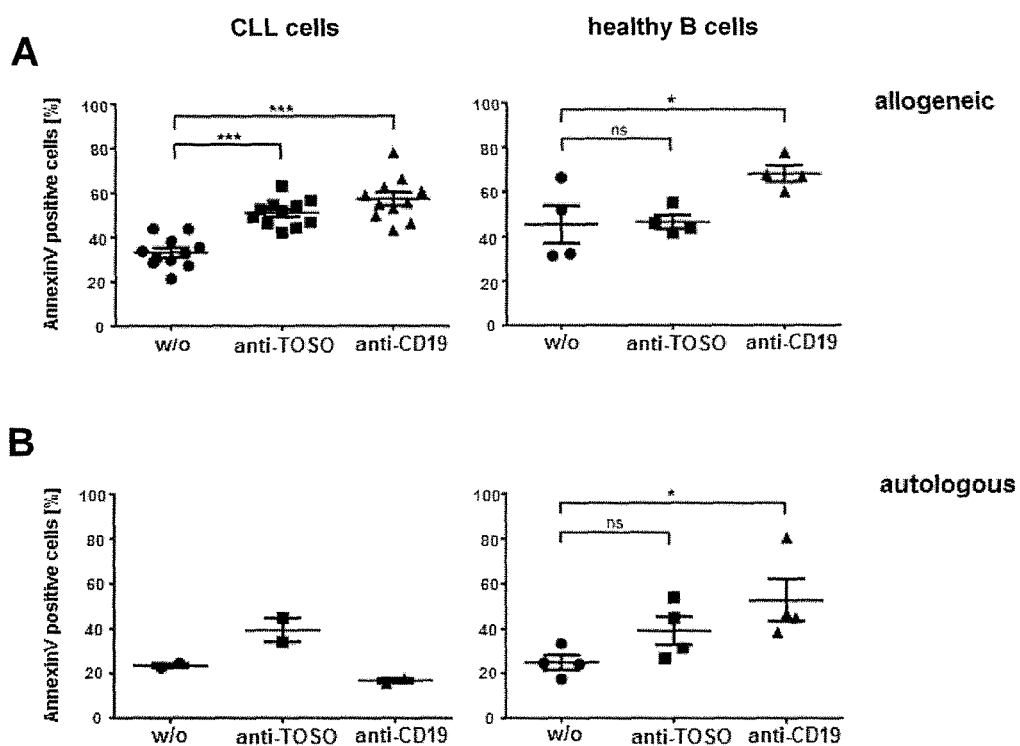
Figure 3:
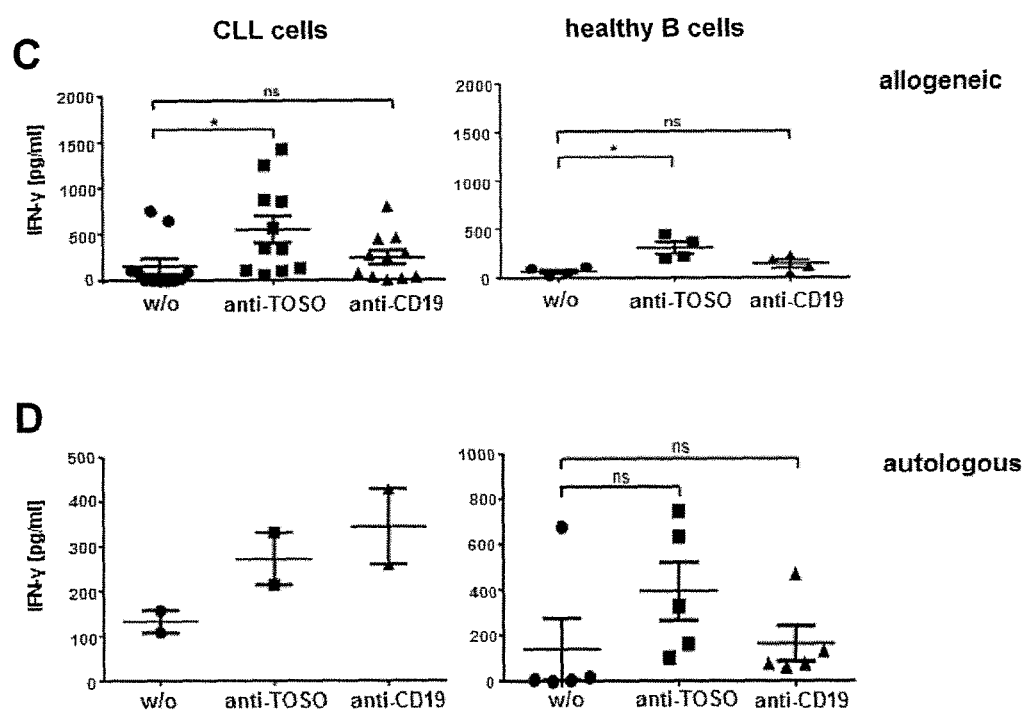

FIG. 3: Specific cytolysis of B-CLL cells by CAR engineered T cells engineered. B-CLL cells were labeled with CFSE (0.83 µM). Unmodified T cells and allogeneic [A] or patient's derived autologous [B] T cells were modified with the anti-TOSO CAR and anti-CD19 CAR, respectively, and co-incubated with B-CLL cells (1×10⁵) for 24 hours. Viability of B-CLL cells was recorded by flow cytometry. Each dot represents an individual B-CLL patient. Apoptotic and dead cells were stained with Annexin V-APC. CAR redirected cytolysis was calculated in comparison to cytolysis by T cells without CAR (w/o). Statistic calculations were based on Student's t-test, * represents $p<0.05$,  represents $p<0.01$, * represents $p<0.001$. n.s. represents not significant. [C, D] B-CLL cells were co-cultivated with CAR engineered allogeneic or autologous T cells and the supernatants were analysed for IFN-γ by ELISA. Each dot represents an individual B-CLL patient. The test was done in triplicates. Statistic calculations were based on Student's t-test, * represents $p<0.05$.

DETAILED DESCRIPTION OF THE PRESENT INVENTION

The inventors aim to provide genetically engineered T-cells containing a chimeric antigen receptor whereby said T-cells display a toxic activity on TOSO⁺ cancer cells while being less or non-toxic to TOSO⁺ non-cancer cells in said subject. That is, in a first aspect, the present invention relates to methods comprising administering T-cells with a chimeric antigen receptor in adoptive cell therapy for treating TOSO⁺ cancer in particular, TOSO⁺ lymphoma or TOSO⁺ leukemia in a subject in need thereof whereby the chimeric antigen receptor contains at least the following domains starting from the N-terminus to the C-terminus: an anti-TOSO single chain antibody domain, in particular derived from the 6B10 anti-TOSO antibody and represented by Seq. ID. No. 2, or a homolog having binding specificity to TOSO thereof having at least 70% identity with SEQ ID No. 2; a transmembrane domain; and a cytoplasmatic signaling domain; optionally a spacer domain between the anti-TOSO single chain domain and the transmembrane domain characterized in that said T-cell with the chimeric antigen receptor initiates or augments an immune response in or is toxic to TOSO⁺ cancer cells, in particular, TOSO⁺ leukemia cells or TOSO⁺ lymphoma cells while, being non-toxic or less toxic to TOSO⁺ non-cancer cells in said subject.

The 6B10 anti-TOSO antibody is described in Pallasch C P, et al., Blood, 2008 Nov. 15; 112(10):4213-9. doi: 10.1182/blood-2008-05-157255.

In this connection, the term "TOSO⁺ cancer cells" refers to malignant cells or neoplastic cells expressing the TOSO molecule.

Further, the term "TOSO⁺ non-cancer cells" refers to benign (healthy) cells expressing the TOSO molecule, like B-cells.

The terms "non-tumor cells" and "tumor cells" as well as "non-cancer cells" and "cancer cells" are used herein interchangeably unless otherwise defined.

The term "non-toxic" and "less toxic" are used herein interchangeably unless otherwise indicated and identifies that the level or amount of non-cancer cells killed by CAR are significant less compared to the level or amount of cancer cells killed by the same CAR.

As used herein, the term "comprise" or "comprising" as well as the terms "contain" or "containing" refers to the embodiment of "consist" or "consisting".

The term "homolog" as used herein refers to molecules, either DNA or polypeptides, having a sequence homology of a certain amount, namely of at least 70%, like at least 80%, 90%, 95%, 96%, 97%, 98%, 99% of the nucleic acid sequence or the amino acid sequence it is referred to. Homology refers to the magnitude of identity between two sequences. Homolog sequences have the same or similar characteristics, in particular, have the same or similar property of the sequence as identified. For example, the homolog of the 6B10 sequence of Seq. ID. No. 2 has the same or similar binding specificity to the TOSO molecule as it is the case for the 6B10 molecule. Further, homologs include nucleic acid molecules encoding the same peptide but may vary in its sequence due to the degeneracy of the genetic code. Further, identity refers to presence of identical amino acid or nucleic acid molecules in the order as described for the sequence it refers to. That is, in case of at least 90% identity, 90% or more of the nucleic acid and amino acid molecules, respectively, are identical at the respective positions. Unless otherwise identified, the terms "homology" and "identity" are used herein interchangeably. In an embodiment, the homolog is a homolog of the 6B10 scFv peptide of SEQ ID No. 2 binding specifically to the same epitope recognized by the 6B10 scFv peptide of SEQ ID No. 2.

In addition, the term "genetically engineered" refers to cells being manipulated by genetic engineering. That is, the cells contain a heterologous sequence which does not naturally occur in said cells. Typically, the heterologous sequence is introduced via a vector system or other means for introducing nucleic acid molecules into cells including liposomes. The heterologous nucleic acid molecule may be integrated into the genome of said cells or may be present extra-chromosomally, e.g. in the form of plasmids. The term also includes embodiments of introducing genetically engineered, isolated CAR polypeptides into the cell.

The term "initiates or augments an immune response to TOSO⁺ cells" refers to embodiments where the immune response of the subject receiving the adoptive cell therapy against these cells is initiated or augmented which can be determined on the basis of cytokine release or cytotoxicity against the TOSO⁺ cells.

Generally, CARs are fusion proteins, consisting of an extracellular antibody type recognition domain fused to intracellular T-cell signaling proteins. Typically, the ectodomain containing the antigen recognition region comprises a signal peptide and an antigen recognition unit. According to the present invention, the ectodomain comprises an anti-TOSO single-chain domain. It is preferred, that said single chain domain is a single chain domain selected from 6B10 scFv of SEQ. ID. No. 2 or a homolog thereof binding specifically to TOSO having at least 70% identity with SEQ ID No. 2. Further, the single chain domain may be derived from other anti-TOSO antibodies like the monoclonal antibodies anti-FAIM3, clone 1E4 of Abnova Corp., or clone OTI1E6 (formerly 1 E6) (TA507395) of Origene Technologies, clone EPR3811 (TA307218) of OriGene Technologies, MAAG745 of Creative BioMart, clone 2F5 of Creative BioMart, mAB A36 and A38 as described in Nguyen X H, et al., Blood. 2011 Jul. 21; 118(3):598-608. doi: 10.1182/blood-2010-10-313643. Said antibodies have similar binding specificity to TOSO as it is the case for the 6B10 antibody, namely binding to TOSO.

The ectodomain may be spaced apart from the transmembrane domain by the presence of a spacer domain. Said optional spacer domain links the antigen-binding domain to the transmembrane domain and it is preferred that said transmembrane domain is flexible enough to allow the antigen binding domain to orient in different directions to facilitate antigen recognition.

The transmembrane domain is typically a hydrophobic alpha helix that spans the membrane. Other transmembrane domains can also be used. Finally, the endodomain represents the signaling domain in the cytoplasmic part of the CAR.

It has been recognized that a T-cell containing the CAR as described, namely, containing a CAR starting from the N-terminus to the C-terminus having the following composition: an anti-TOSO single-chain antibody domain, optionally, a spacer domain, a transmembrane domain, a cytoplasmic domain is able to display immune response activity distinctively between TOSO$^+$ cancer cells and TOSO$^+$ non-cancer cells. Thus, the T-cells of the present invention overcome the problems known in the art of cytotoxic effects on both types of cells, e.g. malignant B leukemia/lymphoma cells and healthy B-cells as described in the art.

In an embodiment of the present invention, the CAR comprises a leader sequence being located N-terminally to the anti TOSO single chain antibody domain.

In addition, in another embodiment, the anti-TOSO single chain antibody domain is a 6B10 scFv peptide, in particular, of SEQ. ID. No. 2. It has been recognized herein that an anti-TOSO single-chain antibody fragment of the variable region (scFv), in particular, of the 6B10 antibody, allows to display the desired activity, namely, being toxic to TOSO$^+$ cancer cells while being non-toxic to TOSO$^+$ non-cancer cells.

In another embodiment, the spacer domain of the CAR molecule is an IgG$_1$ hinge-CH2CH3 domain or a homolog thereof having at least 70% identity with the sequence of SEQ. ID. No. 5 therewith, preferably, the spacer domain is a mutated IgG$_1$ hinge-CH2CH3 domain according to SEQ. ID. No. 5.

In some embodiments, between the spacer domain and the transmembrane domain a linker may be located. For example, in the CAR of Seq. ID. No.4 a linker of 4 amino acids is located between the spacer domain and the transmembrane domain.

Further, another embodiment relates to a T-cell with a chimeric antigen receptor wherein the transmembrane domain is derived from the CD28 molecule, e.g. the transmembrane domain of the CD28 molecule including a short intracellular domain lacking the Ick domain e.g. of SEQ. ID. No. 6

The signaling domain or endodomain or intracellular domain which are used herein interchangeably, contains a CD3 zeta or FcEpsilon receptor (IgE receptor) gamma chain signaling chain and/or a co-stimulatory domain. For example, the intracellular domain is a CD3 zeta signaling domain of SEQ. ID. No. 7 or a homolog thereof having at least 70% homology. In another embodiment, the intracellular domain is the Fc epsilon receptor gamma signaling domain of SEQ. ID. No. 8 or a homolog thereof having at least 70% identity. The signaling domain is responsible for the activation of the immune response activity in T-cells including the cytotoxic activity or interferon-gamma secretion.

The CAR molecule may be a so-called "second generation" CAR molecule. Second generation CAR molecules have improved signaling domains additionally containing a second co-stimulatory signaling domain, e.g. derived from CD28, CD134 (OX40) or CD137 (4-1BB). "Third generation" CAR molecules contain a combined co-stimulatory signaling domain, e.g., CD28 combined with CD137 or CD134.

Further, The CAR molecules may be dual chain CAR. A dual chain CAR consists of two chains, the immunoglobulin light chain and the immunoglobulin heavy chain with their constant regions, whereby the heavy chain is anchored to the membrane and linked to an intracellular signaling domain for T-cell activation. The two chains form a stable heterodimer and bind with high affinity and specifically to their cognate antigen. Thus, activation of the T-cells according to the present invention takes place releasing pro-inflammatory cytokines and for lysing the target cells.

An overview about the CAR molecules is provided e.g. in Gilham D. E. et al., Trends in Molecular Medicine, 2012, 18(7), 377-384.

In a preferred embodiment of the present invention, the T-cell is a T-cell with a chimeric antigen receptor wherein the chimeric antigen receptor is a polypeptide of SEQ. ID. No. 3. Said CAR is also referred to herein as #1389.

The anti-TOSO CAR #1389 is expressed on the surface of T-cells and is composed in the extracellular part of the anti-TOSO single chain fragment of variable region (scFv) antibody 6B10 and the human IgG1 CH2CH3 domain as spacer between scFv and the trans-membrane domain. In an embodiment of the invention, the modification of the IgG1 domain consists of point mutations to convert the wild-type amino acid sequence PELLGGP X$_{13}$ MISRT (Seq. ID. No. 9) to PPVA-GP X$_{13}$ MIART (Seq. ID. No. 10) which reduces unintended binding of the CAR Fc domain to Fc receptors on other cells like innate immune cells which would mediate unintended activation and the activation of the CAR T-cells. The transmembrane and intracellular membrane proximal part of CAR #1389 is derived from human CD28 and is fused to the intracellular part of human CD3zeta. In an embodiment of the invention, the CD28 sequence is mutated at P560>A560, P563>A563, P564>A564 (Kofler et al., Mol. Ther. 19, 760-767 (2011). Thereby the CD28 binding site for the Ick kinase is destroyed with the consequence that activation of the Ick signaling pathway and subsequent CAR mediated IL-2 secretion is prevented. Pre-clinical models imply that Treg cell mediated repression of CAR T-cell effector functions is reduced under these conditions.

As demonstrated in the examples, the T-cells act differently on TOSO$^+$ cells, namely, TOSO$^+$ cancer cells are killed while TOSO$^+$ non-cancer cells remain alive or less numbers are killed in presence of T-cells with #1389 CAR.

As an example, T-cells expressing the #1389 are not toxic against healthy human TOSO$^+$ B cells whereas TOSO$^+$ lymphoma cells are eliminated.

Moreover, as demonstrated in the example, the T-cells containing the #1389 CAR according to the present invention show less or no toxic activity toward healthy human B- and T-cells. No significant autoimmune activity towards autologous healthy cells occurred and no worse side effects are anticipated. In a further aspect, the present invention relates to the use of the T-cell with a chimeric antigen receptor according to the present invention in adaptive cell therapy for treating TOSO$^+$ cancer in a subject in need thereof. For instance the TOSO$^+$ cancer may be B- or T-cell derived leukemia/lymphoma, in particular chronic lymphocytic leukemia, Hodgkin's lymphoma, non-Hodgkin's lymphoma, anaplastic large cell lymphoma, acute lymphocytic leukemia, cutaneous lymphoma, mycosis fungoides, lymphoproliferative diseases, systemic mastocytosis, stem cell derived malignancies, or cancer stem cells or others.

That is, surprisingly T-cells with the chimeric antigen receptor according to the present invention allow to treat TOSO$^+$ cancer in a subject in need thereof without harming the non-cancer TOSO$^+$ cells present in the subject to be treated. In contrast to previous observations with a tremendous variety of CARs having different antigen binding domains, the anti-TOSO antibody domain allows to eliminate malignant TOSO$^+$ cells while benign TOSO$^+$ cells are not or less affected.

In a further aspect, the present invention relates to the polypeptide of SEQ. ID. No. 4 representing the CAR polypeptide denoted #1389 herein, or a homolog thereof having at least 90% identity whereby said polypeptide or its homolog when being expressed in a T-cell is a chimeric antigen receptor displaying a toxic effect on TOSO$^+$ cancer cells while being non-toxic on TOSO$^+$ non-cancer cells. For example, the polypeptide of Seq. ID. No. 4 is encoded by the nucleic acid sequence of Seq. ID. No. 3.

The polypeptide is composed of the 6B10-scFv single chain domain of anti-TOSO antibody, a spacer domain being a IgG1 hinge-CH2CH3 domain, a transmembrane domain derived from CD28, in particular, a CD28 derived transmembrane domain including a proximal intracellular domain, and the intracellular domain of CD3 zeta.

In addition, the present invention provides nucleic acid molecules comprising the nucleic acid sequence encoding the polypeptide according to the present invention. Furthermore, vectors are provided comprising the nucleic acid sequence according to the present invention encoding the polypeptide as described. The skilled person is well aware of suitable vector systems and vectors, in particular, vectors allowing transfection and transduction of eukaryotic cells, in particular, T-cells.

Moreover, the present invention provides a cell, cell line or a host cell containing the vector according to the present invention or a nucleic acid molecule according to the present invention. Preferably, said cell, cell line or host cell is a T-cell, e.g., a CD4$^+$ T-cell or a CD8$^+$ T-cell.

Further, the present invention provides a kit or system containing the vector according to the present invention, the cell, cell line or host cell according to the present invention, or the polypeptide according to the present invention or a nucleic acid molecule according to the present invention or mixtures thereof for use in the production of T-cells expressing the chimeric antigen receptor. The kit or system according to the present invention may contain further components including means for introducing the vector or polypeptide on nucleic acid molecules into the cells. The skilled person is well aware of suitable means for doing so.

The present invention is further described by way of examples. Said examples illustrate the invention further without limiting the same thereto.

EXAMPLES

Preparation of the T-Cells with #1389 CAR

The retroviral vector coding for the #1389 CAR was produced using a Galv pseudotyped envelope. In summary, vector particle production was done transiently on the human embryonic kidney cell line 293T after Polyfect® mediated DNA transfection. Vector particles were pseudotyped with Galv. No vector titer was determined.

Transduction of human blood lymphocytes was done according to standard techniques (Cheadle, E. J., et al., Chimeric antigen receptors for T-cell based therapy. Chapter 36, in: "Antibody engineering: methods and protocols", 2nd Edition, Ed. P. Chames, Meth. Mol. Biol. 907, 645-666 (2012), doi: 10.1007/978-1-61779-974-7_36). The CAR #1389 was expressed by human T-cells as measured at day 2 by flow cytometry using an antibody directed to the extracellular IgG1 CH2 CH3 domain of the CAR. For comparison the anti-CD19 CAR as described in Koehler, P., et al., Adv. Hematol., 2012, article ID 595060, doi:10.1155/2012/595060, (2012) was expressed on human T-cells as measured by the same procedure.

Example 1: Activity of CAR #1389 Modified T-Cells Toward TOSO$^+$ Tumor and Healthy Cells Engineering of T-Cells with CAR #1389

Figure 1:
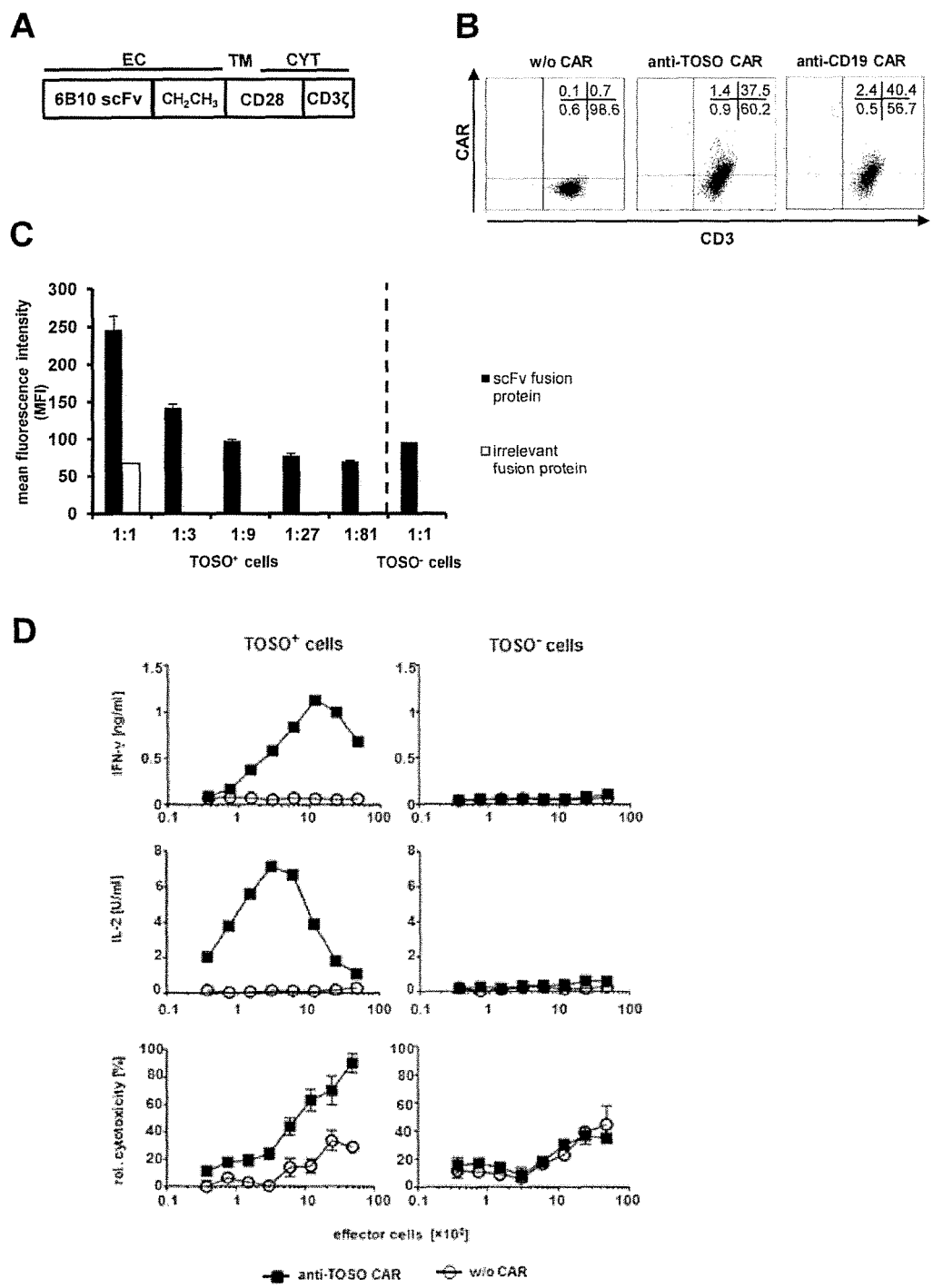
FIG. 1: T cells with TOSO-specific CAR recognize and kill TOSO+ cells. [A] Schematic diagram depicting the modular composition of the anti-TOSO CAR used in this study. The expression cassette contains the DNA coding for the anti-TOSO scFv (derived from the hybridoma cell line 6B10) fused to DNA coding for the hinge-CH2CH3 region of the human IgG1, transmembrane CD28 domain and the intracellular CD28 and CD3ζ domain for signaling. [B] CAR expression on the surface of T cells. Human peripheral blood T cells were engineered by retroviral gene transfer with the respective CAR and cultured in presence of 500 U/mL IL-2. CAR expression was detected by flow cytometry after 48 hours using the PE-conjugated anti-human-IgG1 antibody which binds to the extracellular CAR IgG1 domain and with the FITC-conjugated anti-CD3 antibody to identify T cells. Non-modified T cells (w/o CAR) were used as control. Numbers represent the percentage of T cells which express the CAR on the surface in comparison to the total number of T cells. [C] Anti-TOSO scFv domain specifically binds to TOSO positive tumor cells. TOSO-positive and TOSO-negative tumor cells ($2\times10^5$ cells) were incubated with the anti-TOSO scFv-Fc fusion protein (in serial dilutions) and an irrelevant scFv-Fc fusion protein (start concentration 0.025 µg/ml), respectively. Bound protein was detected by flow cytometry after 30 minutes using the PE-conjugated anti-human-IgG1 antibody which binds to the IgG1 Fc domain. Data represent the mean fluorescence intensity (MFI). Each bar represents the mean of three samples±standard deviation. [D] CAR-redirected T cell activation and cytolysis is antigen specific. Peripheral blood T cells were engineered with the anti-TOSO CAR and cocultivated with TOSO-engineered and TOSO-negative HEK293 cells ($1.5\times10^4$ cells/well) at the indicated number of T cells (effector cells). Non-modified T cells (w/o CAR) served as control. Cytotoxicity of tumor cells was determined by the XTT-based viability assay. IFN-γ and IL-2 in the culture supernatant were determined by enzyme-linked immunosorbent assay (ELISA). Data represent the mean of three samples±standard deviation.

Engraftment of human peripheral T-cells with the #1389 CAR was assessed by two color flow cytometry 12 hrs after transduction. FIG. 1B shows a dot blot analysis of CAR engineered T-cells. The number of T-cells with #1389 CAR expression was 37.5% of all T-cells (FIG. 1B).

T-Cell Activation by the CAR #1389

T-cells engineered with the #1389 CAR bind specifically to TOSO expressing 293 cells and become activated indicated by increased secretion of cytokines including IFN-γ and IL-2, by increase in proliferation and in cytolysis of TOSO$^+$ target cells (FIG. 1D). Activation of the T-cells #1389 is antigen-specific as defined by the specificity of the CAR since TOSO$^-$ 293 cells do not trigger T-cell activation.

TOSO Expression on Leukemia and Healthy Cells.

Figure 2:
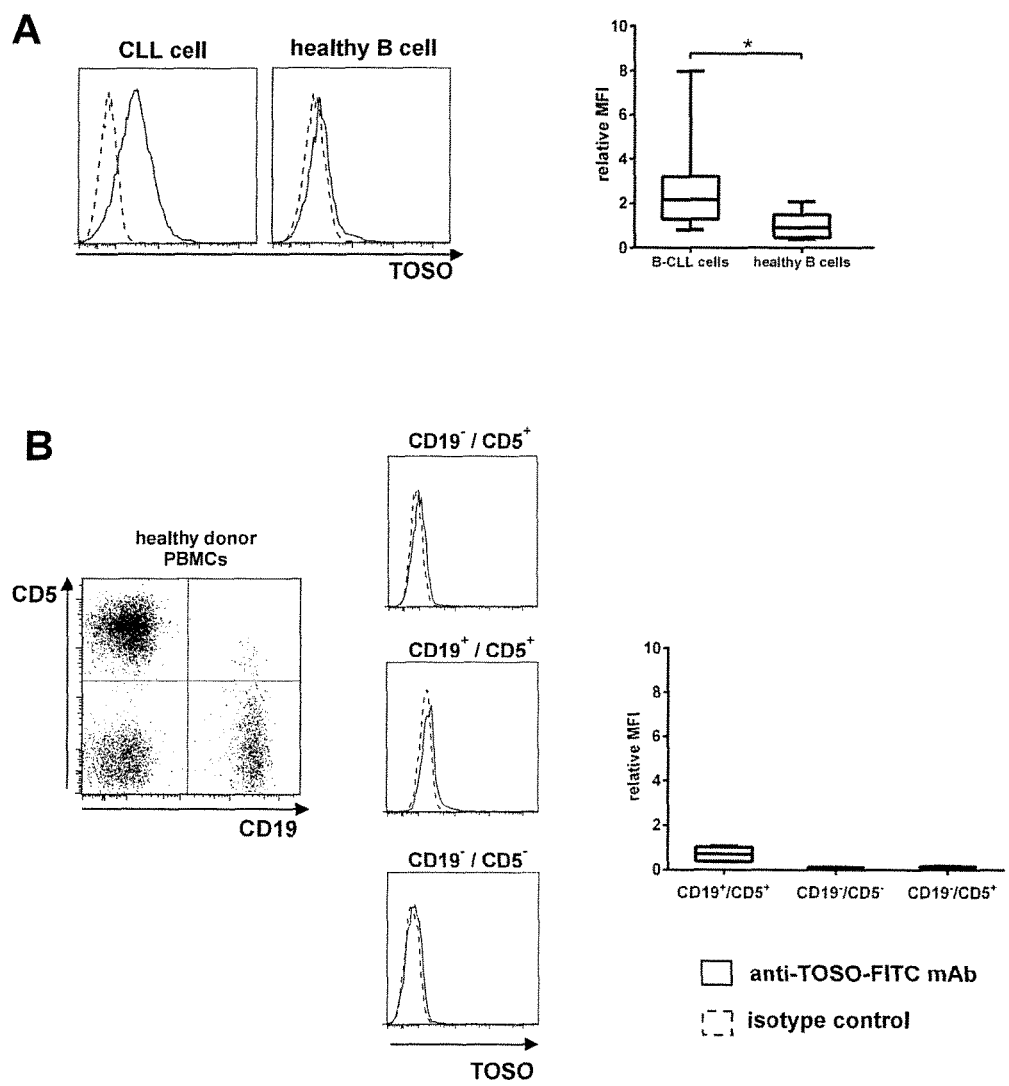
FIG. 2: TOSO is highly expressed by CLL cells compared to healthy B cells [A] Primary CLL cells (n=14) and healthy donor B cells (n=8) were stained by the FITC-conjugated anti-TOSO mAb 6B10 (solid black line) or an isotype-matched control antibody (dotted line) and recorded by flow cytometry. Statistical analysis was performed using the Student's t-test (*p=0.03). The histograms show the analyses of cells of a representative healthy donor and a CLL patient.

B-CLL cells from leukemia patients and B cells from healthy donors were recorded by flow cytometry for TOSO using the 6B10 antibody (FIG. 2A, B). Staining for CD5 and CD19 identified B-CLL cells. The level of TOSO was in average higher in B-CLL cells of leukemia patients than of B-cells of healthy donors.

Redirected Toxicity of T-Cells with #1389 CAR Towards TOSO$^+$ B-CLL Leukemia Cells Versus Healthy B Cells.

TOSO$^+$ B-CLL leukemia cells were co-incubated with T-cells engineered with anti-TOSO CAR #1389. As controls same TOSO$^+$ cells were co-incubated with T-cells without CAR. CLL cells and T-cells were derived from the same donor (autologous cells) or T-cells were derived from a healthy donor (allogeneic cells).

The total number of target cells was determined by FACS and standardized by using a counting standard. Dead cells were identified by staining with Annexin V. B-CLL cells were stained with 0.83 μM CSFE prior co-incubation. The test was done in triplicates and the data are summarized in FIG. 3A,B. To determine toxicity of T-cells CAR #1389 against TOSO$^+$ healthy and tumor cells, the number of dead CSFE stained B-CLL cells was determined by means of flow cytometry. T-cells with anti-TOSO CAR increased the number of dead B-CLL cells, indicated by increase in Annexin V positive, CSFE positive cells. This was the case with allogeneic and autologous CLL cells. The same result was obtained with anti-CD19 CAR T-cells. Accordingly, anti-TOSO CAR T-cells were induced to release IFN-γ upon co-incubation with allogeneic and autologous CLL cells (FIG. 3C, D). Anti-TOSO CAR T-cells did not eliminate co-incubated healthy (allogeneic or autologous) B cells while anti-CD19 CAR T-cells did (FIG. 3A, B). Anti-TOSO CAR T-cells released some IFN-γ in the co-incubation with allogeneic B cells which is due to an allo-response and was not increased in the autologous situation.

CONCLUSIONS

The toxicity of T-cells with the anti-TOSO CAR #1389 against healthy human TOSO$^+$ leukemia cells was tested in comparison to targeting TOSO$^+$ healthy B cells. T-cells from healthy donors as well as from patients were engineered to express the #1389 CAR and T-cells without CAR from the same transduction batch were used. We recorded toxicity of T-cells #1389 towards TOSO$^+$ CLL cells while no substantial toxicity towards healthy B cells. No specific toxicity of non-engineered T cells towards TOSO+ leukemia cells was recorded. In contrast T cells engineered with the anti-CD19 CAR were toxic towards B-CLL cells and healthy B-cells.

Embodiments

1. T-cell with a chimeric antigen receptor for use in adoptive cell therapy for treating TOSO$^+$ cancer in particular, TOSO$^+$ leukemia or TOSO$^+$ lymphoma, in a subject in need thereof whereby the chimeric antigen receptor contains at least the following domains starting from the N-terminus to the C-terminus: an anti-TOSO single chain antibody domain, in particular, 6B10 scFv of SEQ. ID. No.2 or a homolog thereof binding specifically to TOSO having at least 70% identity with SEQ. ID. No. 2; optionally a spacer domain; a transmembrane domain; and a cytoplasmatic signaling domain; characterized in that said T-cell with the chimeric antigen receptor initiates or augments the immune response to or is toxic to TOSO$^+$ cancer cells, in particular, TOSO$^+$ leukemia cells or TOSO$^+$ lymphoma cells, while being less or non-toxic to TOSO$^+$ non-cancer cells in said subject.
2. The T-cell with a chimeric antigen receptor for use in adoptive cell therapy for treating TOSO$^+$ cancer in a subject in need thereof according to embodiment 1 further comprising a leader sequence being located N-terminally to the anti-TOSO single chain antibody domain.
3. The T-cell with a chimeric antigen receptor for use in adoptive cell therapy for treating TOSO$^+$ cancer in a subject need thereof according to any one of embodiments 1 to 2 wherein the anti-TOSO single chain antibody domain is the 6B10 scFv peptide of SEQ ID No. 2, or a homolog thereof binding specifically to the same epitope, recognized by the 6B10 scFv peptide of SEQ ID No. 2.
4. The T-cell with a chimeric antigen receptor for use in adoptive cell therapy for treating TOSO$^+$ cancer in a subject in need thereof according to any one of embodiments 1 to 3 wherein the spacer domain is an IgG$_1$ CH2CH3 domain or a homolog thereof having at least 70% identity with the sequence of Seq. ID. No. 5, preferably, the spacer domain is a mutated IgG$_1$ CH2CH3 domain according to SEQ. ID. No. 5.
5. The T-cell with a chimeric antigen receptor for use in adoptive cell therapy for treating TOSO$^+$ cancer in a subject need thereof according to any one of the preceding embodiments wherein the trans-membrane domain is derived from CD28.
6. The T-cell with a chimeric antigen receptor for use in adoptive cell therapy for treating TOSO$^+$ cancer in a subject in need thereof according to any one of the preceding embodiments wherein the intracellular domain contains a CD3zeta or a FcepsilonRIgamma signaling chain and/or a costimulatory domain, like wherein the intracellular domain is the CD3 zeta signaling domain of SEQ. ID. No. 7 or a homolog thereof having at least 70% homology or like wherein the intracellular domain is the Fc epsilon receptor gamma-signaling domain of SEQ. ID. No. 8 or a homolog thereof having at least 70% homology.
7. The T-cell with a chimeric antigen receptor for use in adoptive cell therapy for treating TOSO$^+$ cancer in a subject in need thereof according to any one of the preceding embodiments wherein the intracellular domain is the CD28 signaling domain, in particular a CD28 domain lacking the lck binding motif, like the domain present in Seq. ID. No. 6.
8. T-cell with a chimeric antigen receptor for use in adoptive cell therapy for treating TOSO$^+$ cancer in a subject in need thereof according to any one of the preceding embodiments, wherein the chimeric antigen receptor is a polypeptide of SEQ. ID. No. 4
9. The T-cell with a chimeric antigen receptor for use in adoptive cell therapy for treating TOSO$^+$ cancer in a subject need thereof according to any one of the preceding embodiments wherein the TOSO$^+$ cancer is any one of leukemia or lymphoma, in particular chronic lymphocytic leukemia, Hodgkin's lymphoma, non-Hodgkin's lymphoma, anaplastic large cell lymphoma, acute lymphocytic leukemia, cutaneous lymphoma, mycosis fungoides, lymphoproliferative diseases, systemic mastocytosis, or stem cell derived malignancies or cancer stem cells.
10. A polypeptide of SEQ. ID. No. 4 or a homolog thereof having at least 90% identity whereby said polypeptide when being expressed in a T-cell as a chimeric antigen receptor display a toxic effect on TOSO$^+$ cancer cells while being less-toxic on TOSO$^+$ non-cancer cells.
11. A nucleic acid molecule comprising a nucleic acid sequence encoding the polypeptide of embodiment 10, like the nucleic acid sequence of Seq. ID. No. 3.
12. A vector comprising the nucleic acid sequence according to embodiment 11.
13. A cell, cell line or a host cell containing a vector according to embodiment 12 or a nucleic acid molecule according to claim 11.
14. A kit or system containing a vector according to embodiment 12, a cell, cell line or a host cell according to embodiment 13, the nucleic acid molecule according to embodiment 11 and/or the peptide of embodiment 10 for use in the production of T-cells expressing the chimeric antigen receptor.
15. A chimeric antigen receptor as defined in any one of embodiments 1 to 8 for use to improve persistence and amplification of a genetically engineered lymphocyte expressing said chimeric antigen receptor.

The invention claimed is:

1. A method for treating TOSO+ cancer in a subject in need thereof by adoptive cell therapy including the step of administering T-cells with a chimeric antigen receptor whereby the chimeric antigen receptor contains at least the following domains starting from the N-terminus to the C-terminus: an anti-TOSO single chain antibody domain; a transmembrane domain; and a cytoplasmic signaling domain; optionally a spacer domain between the anti-TOSO single chain antibody domain and the transmembrane domain, whereby the T-cells with the chimeric antigen receptor initiates or augments the immune response to or is toxic to TOSO+ cancer cells while being less or non-toxic to TOSO+ non-cancer cells in said subject, wherein the transmembrane domain is derived from a human CD28, and wherein the cytoplasmic signaling domain contains at least one domain selected from the group consisting of a human CD3 zeta signaling domain, a human Fc epsilon receptor gamma-signaling domain, and a human CD28 signaling domain lacking the lck binding motif.

2. The method for treating TOSO+ cancer in a subject in need thereof by adoptive cell therapy according to claim 1, wherein the TOSO+ cancer is TOSO+ leukemia or TOSO+ lymphoma.

3. The method for treating TOSO+ cancer in a subject in need thereof by adoptive cell therapy according to claim 1, wherein the anti-TOSO single chain antibody domain is the 6B10 scFv peptide as set forth in SEQ ID NO: 2.

4. The method for treating TOSO+ cancer in a subject in need thereof by adoptive cell therapy according to claim 1, further comprising a leader sequence being located N-terminally to the anti-TOSO single chain antibody domain.

5. The method for treating TOSO+ cancer in a subject in need thereof by adoptive cell therapy according to claim 1, wherein the spacer domain is a mutated $IgG_1$ CH2CH3 domain as set forth in SEQ ID NO: 5.

6. The method for treating TOSO+ cancer in a subject in need thereof by adoptive cell therapy according to claim 1, wherein the cytoplasmic signaling domain contains at least one domain selected from the group consisting of the human CD3 zeta signaling domain having the sequence as set forth in SEQ ID NO: 7, and the human Fc epsilon receptor gamma-signaling domain having the sequence as set forth in SEQ ID NO: 8.

7. The method for treating TOSO+ cancer in a subject in need thereof by adoptive cell therapy according to claim 1, wherein the cytoplasmic signaling domain is the human CD28 signaling domain lacking the lck binding motif having the sequence as set forth in SEQ ID NO: 6.

8. The method for treating TOSO+ cancer in a subject in need thereof by adoptive cell therapy according to claim 1, wherein the chimeric antigen receptor is the polypeptide as set forth in SEQ ID NO: 4.

9. The method for treating TOSO+ cancer in a subject in need thereof by adoptive cell therapy according to claim 1, wherein the TOSO+ cancer is any one of leukemia or lymphoma, in particular chronic lymphocytic leukemia, Hodgkin's lymphoma, non-Hodgkin's lymphoma, anaplastic large cell lymphoma, acute lymphocytic leukemia, cutaneous lymphoma, or stem cell-derived malignancies or cancer stem cells.

10. The method of claim 6, wherein the cytoplasmic signaling domain further comprises a costimulatory domain.

* * * * *